US005411173A

United States Patent [19]

Weinstein

[11] Patent Number: 5,411,173

[45] Date of Patent: May 2, 1995

[54] COUNTER ATTACHMENT FOR PRODUCT DISPENSERS

[76] Inventor: Albert Weinstein, 9070 Tracy Ct. 3, Boca Raton, Fla. 33496

[21] Appl. No.: 168,143

[22] Filed: Dec. 17, 1993

[51] Int. Cl.$^6$ ..... B67D 5/22

[52] U.S. Cl. ..... 222/38; 222/32; 222/162

[58] Field of Search ..... 222/32, 36, 38, 162; 235/114, 117 A

[56] References Cited

U.S. PATENT DOCUMENTS 1,280,658 10/1918 Byrd ..... 222/38
2,455,962 12/1948 Wheeler et al. ..... 222/38
3,119,557 1/1964 Chapman ..... 235/91
3,606,084 9/1971 Morrone ..... 222/38
4,817,822 4/1989 Rand et al. ..... 222/38
5,020,527 5/1991 Dessertine ..... 128/200.23

FOREIGN PATENT DOCUMENTS 884015 7/1953 Germany ..... 222/38
1423357 2/1976 United Kingdom ..... 222/36
2036695 7/1980 United Kingdom ..... 222/38

*Primary Examiner*—Andres Kashnikow
*Assistant Examiner*—Joseph A. Kaufman
*Attorney, Agent, or Firm*—Oltman and Flynn

[57] ABSTRACT

A counter device attachment for a depressible spray dispenser for products such as medicine. The dispenser comprises a clip to fit about the side wall of the dispenser's casing, a foot-leg positioned beneath the dispenser and connected to the clip, and a counter actuated by the shaft which moves within a shaft housing, wherein a button on the counter is incremented each time the tank is depressed. The length of the vertical shaft is adjustable by controlling the rotation of the top end of the shaft which is mateably threaded to the bottom end of the shaft. The bottom end of the shaft can be threaded within the top end of the shaft or vice-versa. The clip can alternatively be curved or have a dimpled surface which may contact another dimple through a hole in the side of the dispenser. A second embodiment features the counter located beneath the dispenser which is also incremented each time the tank is depressed.

18 Claims, 3 Drawing Sheets

COUNTER ATTACHMENT FOR PRODUCT DISPENSERS

The present invention relates generally to a counter device for a product dispenser and more particularly to a counter mechanism for measuring the number of times a depressible spray dispenser for products such as medicine is depressed.

BACKGROUND OF THE INVENTION

It is well known to dispense fluid or spray medication or perfume by depressing a tank holding the fluid. The tank is housed in a casing. Generally there are directions for the medication that recommend the number of measured dosages which are to be used. Keeping track of these dosages can be difficult. For example, if a medicine is to be used four (4) times a day, the patient may forget how many dosages were used by the middle of the day. Further, the medicine may have a limitation as to the number of times it should be used. Clearly the user must keep track of these dosages.

Thus, the need exists for counting the times a depressible dispenser of fluid is depressed.

The inventor is not aware of any prior art which can attach to an existing spray dispenser and adequately count the number of times the dispenser is depressed. U.S. Pat. No. 5,020,527 to Dessertine describes an inhaler device with a counter/timer means. However, this patent only describes creating a specific housing for an inhaler. Dessertine does not describe his device as an attachment for existing product dispensers. But instead, Dessertine requires that a new housing be created for an inhaler dispenser in order to use his counter.

SUMMARY OF THE INVENTION

The present invention overcomes the above-stated problems, as well as others, as may be determined by a fair reading and interpretation of the entire specification.

In accordance with the invention, there is provided a counter attachment for spray dispensers that can be attached to existing product dispensers which dispense measured amounts of products such as medicine.

In accordance with a first embodiment, the counter attachment includes a clip able to fit about the side wall of a dispenser.

In accordance with another feature, the clip can further include a curved or dimpled surface.

In accordance with another feature, the clip can further include a dimpled surface which may contact a similar dimpled surface on a shaft housing.

In accordance with another feature, the counter attachment further includes a vertical shaft within the shaft housing.

In accordance with another feature, the length of the vertical shaft is adjustable by controlling the rotation of one end of the shaft which is mateably threaded to another end of the shaft. The bottom end of the shaft can be threaded within the top end of the shaft or vice-versa.

In accordance with another feature, the counter attachment further includes a visible counter with an index button which is actuated by the shaft which shows the number of times the dispenser is depressed.

In accordance with another feature, the counter attachment further includes a reset button.

In accordance with another feature, the counter attachment includes foot-leg positioned beneath the dispenser.

In accordance with a second embodiment, the counter further includes locating the counter beneath the dispenser.

Further objects and advantages, and features of the invention will become apparent to those skilled in the art from the following detailed description of a presently preferred embodiment which is illustrated schematically in the accompanying drawings.

DETAILED DESCRIPTION OF THE INVENTION

Before explaining the disclosed embodiment of the present invention in detail it is to be understood that the invention is not limited in its application to the details of the particular arrangements shown since the invention is capable of other embodiments. Also, the terminology used herein is for the purpose of description and not of limitation.

For example, although the fluid referred to above is listed as medicine, the invention has applicability to any type of fluid or spray which is dispensed in a like manner in repeatable similar amounts.

Further, the shapes and appearance of the dispenser components and clip attachment are for illustration only and are modifiable for different types of spray dispensers.

Further, the materials used for construction of the components for the counter attachments can be metal, plastic, metal-plastic or variations thereof.

First Preferred Embodiment

Figure 1:
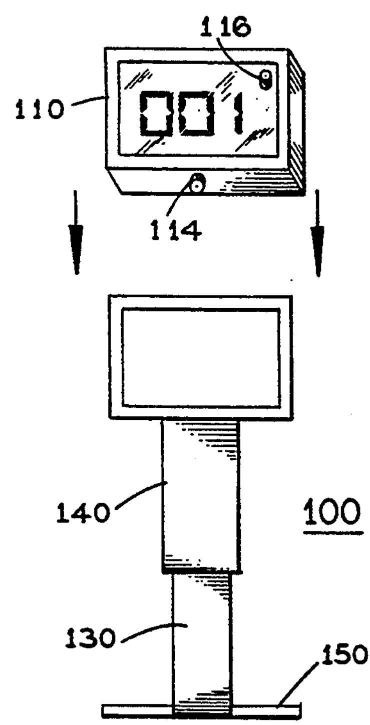
FIG. 1 is an exploded view of the first preferred embodiment of the counter attachment.
Figure 1A:
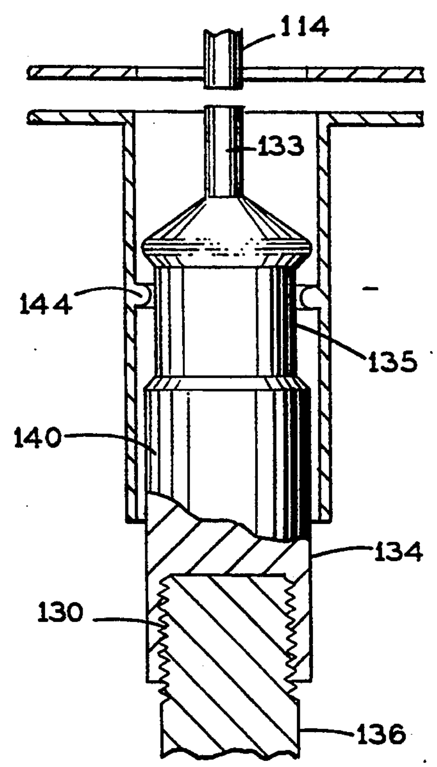
FIG. 1*a* is an exploded view of the shaft portion of the counter attachment shown in FIG. 1.

FIG. 1 is an exploded view of the first preferred embodiment of the counter attachment 100 comprising a counter with reset button 116 and index button 114. When the reset button 116 is depressed by the user the counter 110 reverts back to zero. When the index button 114 is depressed the counter 110 increments one number at a time. The counters that can be used are of well known design and can be displayed as an LCD readout or alternatively can be a mechanical type clicker mechanism.

Counter attachment 100 further comprises a two piece vertical shaft 130 which has a top end 134 that extends into shaft housing 140. The inner walls of the shaft housing 140 include a raised ringed surface 144 which enables the shaft 130 to slide along a length caused by an indentation 135 on the top end 134 of shaft 130. The top of the shaft depicted as 133 contacts the index button 114 on the counter when shaft 130 moves upward. Top end 134 of shaft 130 is mateably connected by threads to a bottom end portion 136 of the shaft 130. The length of the vertical shaft is adjustable by controlling the rotation of the bottom end 136 of the shaft 130 to fit the various sizes of fluid dispensers. The bottom end of the shaft can be threaded within the top end of the shaft or vice versa. Counter attachment 100 further comprises a foot-leg 150 which is connected to the bottom end 136 of shaft 130.

Figure 2:
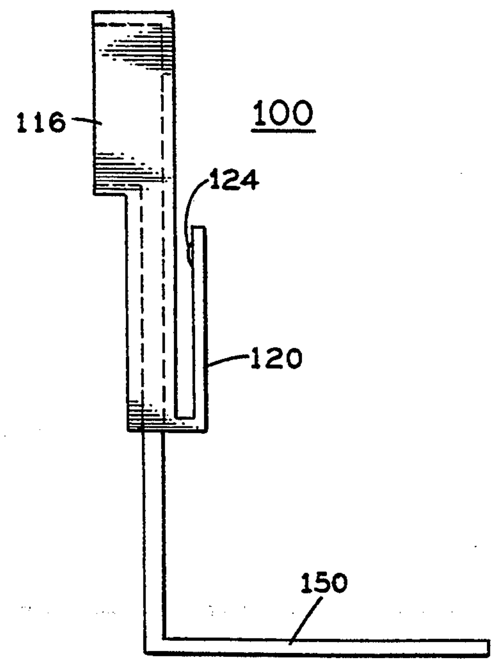
FIG. 2 is a side view of the embodiment of FIG. 1 with a curved clip.
Figure 3:
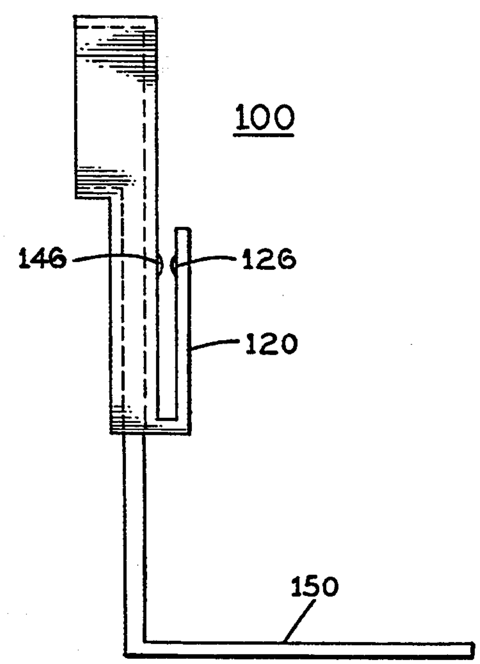
FIG. 3 is a side view of the embodiment of FIG. 1 with a dimpled clip.

FIG. 2 is a side view of the counter attachment 100 of FIG. 1 with a curved portion 124 on clip 120. FIG. 3 is a side view of the counter attachment 100 of FIG. 1 with dimpled areas 126 on clip 120 and an optional dimpled area 146 on shaft housing 140.

Figure 4:
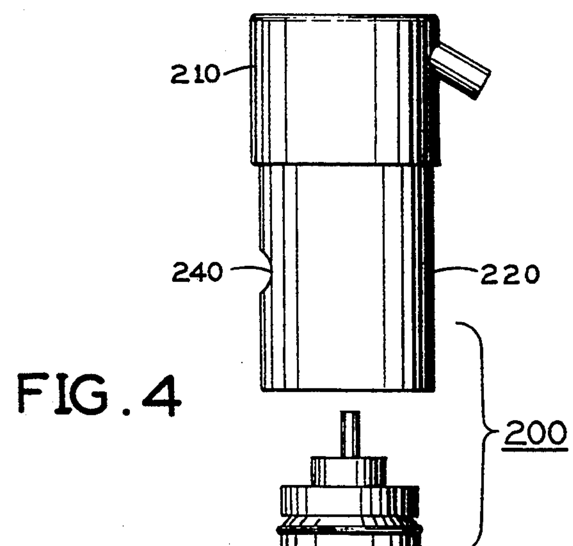
FIG. 4 is a break-away view of the fluid dispenser where the fluid tank is inserted within the dispenser casing.

FIG. 4 is an exploded view of a well known fluid dispenser 200 where the fluid tank 230 is inserted within the dispenser casing 220. The dispenser cap 210 has a nozzle type opening which dispenses the fluid in the tank when the tank is depressed. These types of dispensers are well known for dispensing measured dosages of medicine or perfume or the like. The tank 230 can be pressurized or kept at normal atmospheric pressure. Some casings may have openings 240 in the side which can be used with the dimples of FIG. 3.

Figure 5:
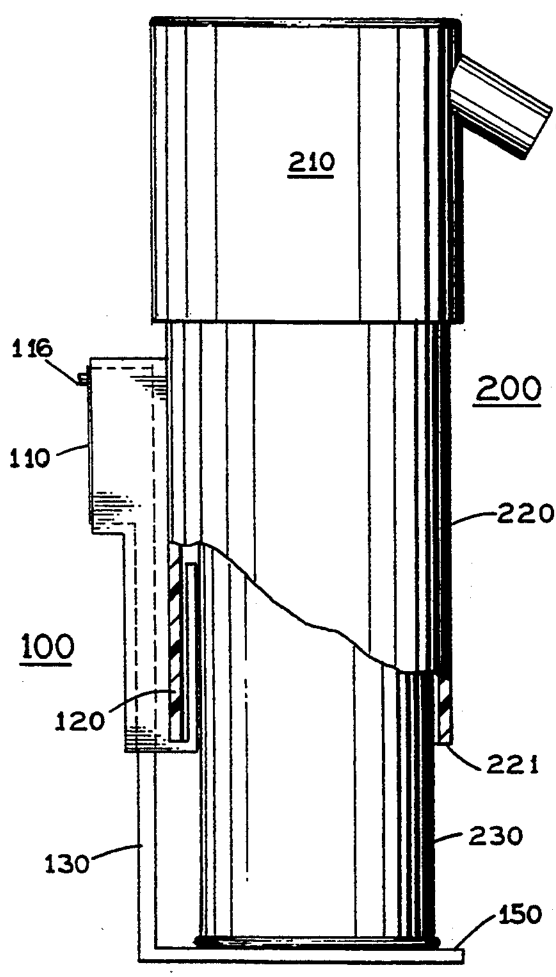
FIG. 5 is a side view of the counter attachment of FIG. 1 attached to the fluid dispenser of FIG. 4.
Figure 6:
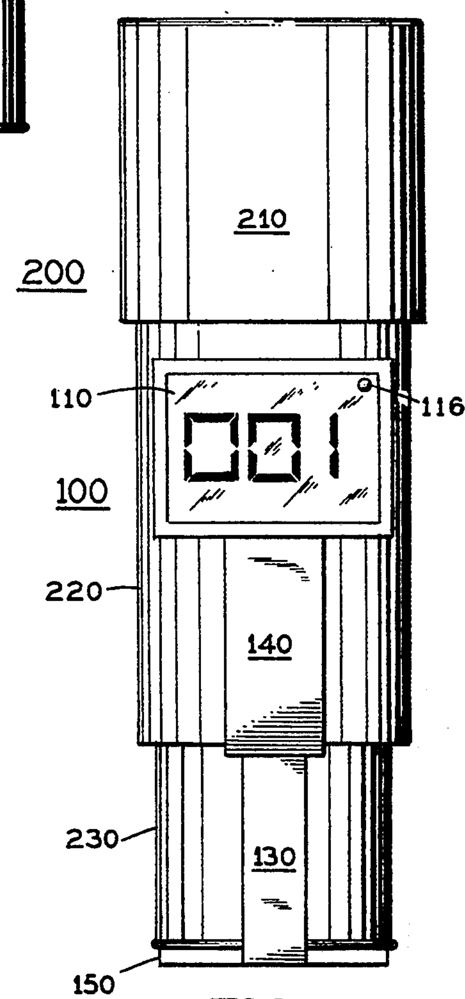
FIG. 6 is a view of the counter.

Assembling the first preferred embodiment will now be discussed in reference to FIGS. 5 and 6. First, the clip 120 of the counter attachment 100 is inserted in the space between tank 230 and casing wall 220. The curved portion 124 or the dimpled portion 126 on clip 120 creates a snug fit. If the casing has openings in its walls as shown by 240 in FIG. 4, then the dimple 126 will contact dimple 146 by passing through these openings when using the clip of FIG. 3.

Next, the length of the vertical shaft 130 is adjusted by rotating the lower end 136 with the top end 134 causing the foot-leg 150 to abut against the bottom of liquid tank 230.

The operation of the first preferred embodiment will now be discussed. FIG. 5 is a side view of the counter attachment of FIG. 1 attached to the fluid dispenser of FIG. 4. FIG. 6 is a front view of FIG. 5. When the tank 230 is depressed, the leg 150 pushes up. This action causes rod 135 to slid up pushing the index button 114 on counter 110 to contact button 114, wherein the counter is incremented by one digit. This operation takes place each time the dispenser is used.

Second Preferred Embodiment

Figure 7:
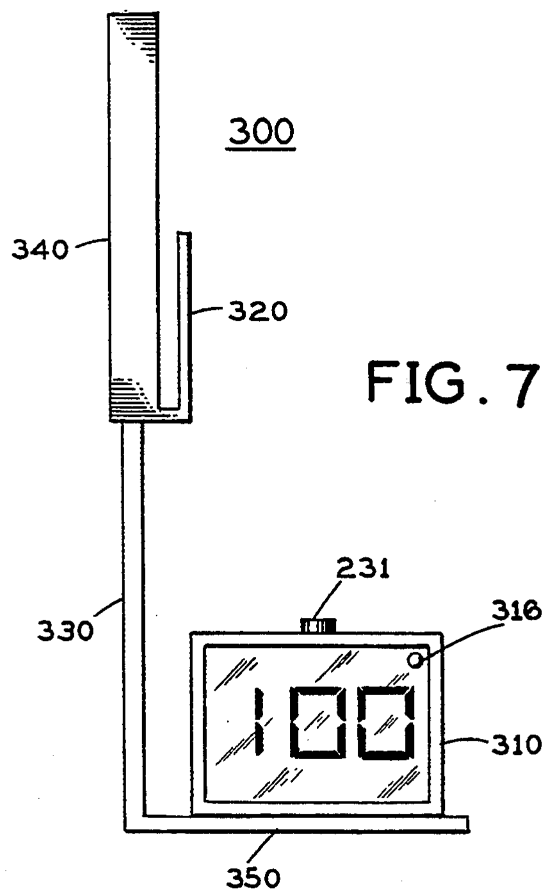
FIG. 7 is a side view of the second preferred embodiment of the counter attachment.
Figure 8:
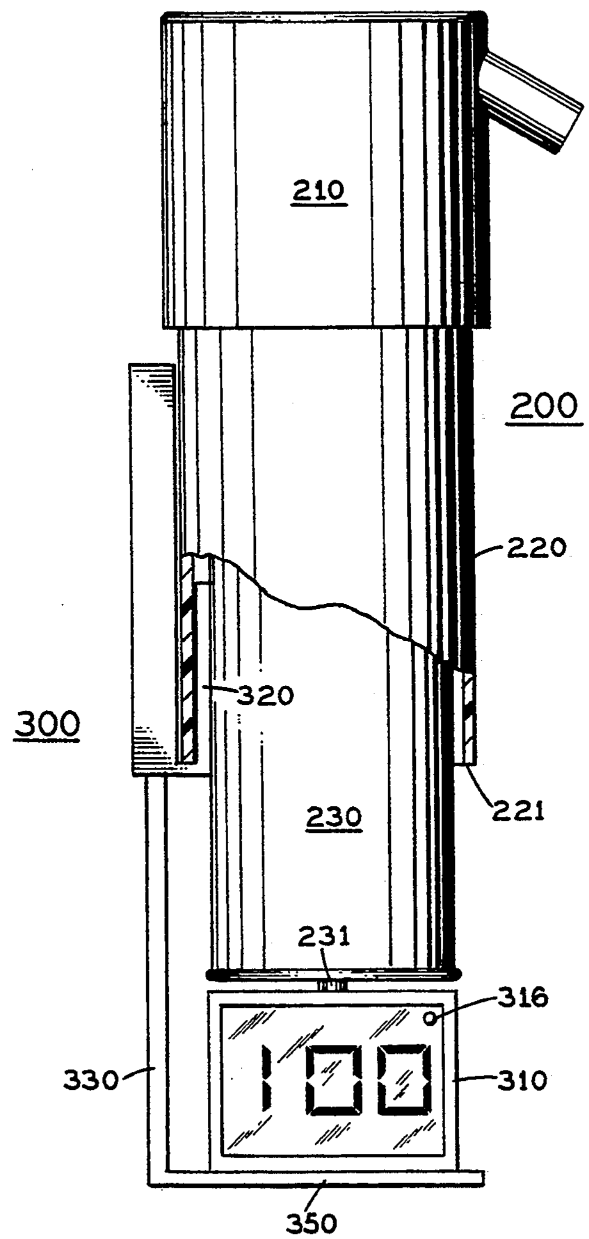
FIG. 8 is a side view of the counter attachment of FIG. 7 attached to the dispenser of FIG. 4

In FIG. 7, the counter 310 is located on the foot-leg 350. Similar to the first embodiment, the counter 310 has reset button 316 and an indexing button 231. The vertical shaft 330, shaft housing 340 and clip 320 are similar to and work in the same way as their counterparts in the first preferred embodiment. FIG. 8 is a side view of the counter attachment 300 of FIG. 7 attached to the fluid dispenser 200 of FIG. 4.

The operation of the second preferred embodiment will now be discussed. When the tank 230 and foot-leg 350 are depressed, the foot-leg 350 pushes the counter against the tank 230. This causes contact with the index button 231 on counter 310, so that the counter is incremented by one digit. This operation takes place each time the fluid dispenser is used.

While tile invention has been described, disclosed, illustrated and shown in various terms or certain embodiments or modifications which it has assumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

I claim as my invention:

1. A counter attachment for a fluid dispenser, the dispenser includes a fluid tank with a top portion extending into a hollow casing and abutting against a dispenser cap, the container having a bottom portion extending beneath the bottom of the casing, the counter attachment comprising;

a clip with a first end and second end, the first end contacting an inner side of the casing;

a shaft housing connected to the second end of the clip;

a counter;

a vertical shaft with top end extending into the shaft housing and a bottom end extending below the shaft housing;

a foot-leg positioned beneath the fluid tank and connected to the bottom end of the vertical shaft; and an indexing button which is located between the fluid tank and the foot-leg, wherein the button abuts against the bottom of the fluid tank and is depressed each time the tank and foot-leg is depressed, wherein depressing the tank and foot-leg increments the counter.

2. The counter attachment of claim 1, wherein the counter further includes:

a reset button.

3. The counter attachment of claim 1, wherein the vertical shaft further includes:

threads on the top end that contact mating threads on the bottom end, which enables the length of the vertical shaft to be adjustable.

4. The counter attachment of claim 1, wherein the vertical shaft further includes:

an area of indentation on the top end of the shaft which moves about a ringed area inside the shaft housing.

5. The counter attachment of claim 1, wherein the clip further includes:

a curved portion.

6. The counter attachment of claim 1, wherein the clip further includes:

a dimple portion.

7. The counter attachment of claim 1, further comprising:

a dimple on the clip abutting toward a dimple on the shaft housing.

8. The counter attachment of claim 7, further including:

an opening in the casing which allows the dimple on the clip and the dimple on the shaft to contact one another.

9. The counter attachment of claim 1, wherein the dispenser is for medication.

10. The counter attachment of claim 1, wherein the dispenser is for spray.

11. A counter attachment for a liquid dispenser, the dispenser includes a fluid tank with a top portion extending into a hollow casing and abutting against a dispenser cap, the container having a bottom portion extending beneath the bottom of the casing, the counter attachment comprising;

a clip with a first end and second end, the first end having a curved portion, contacting an inner side of the casing;

a shaft housing connected to the second end of the clip;

a vertical shaft with it top end extending into the shaft housing and a bottom end extending below the shaft housing;

a foot-leg positioned beneath the fluid tank and connected to the bottom end of the vertical shaft; and a counter having an indexing button which is contacted by the top end of the vertical shaft each time the dispenser top is depressed.

12. The counter attachment of claim 11, wherein the vertical shaft further includes:

threads on the top end that contact mating threads on the bottom end, which enables the length of the vertical shaft to be adjustable.

13. The counter attachment of claim 11, further including:

a dimple on the clip abutting toward an opening in the casing to contact a dimple on the shaft housing.

14. A counter attachment for a fluid dispenser, the dispenser includes a fluid tank with a top portion extending into a hollow casing and abutting against a dispenser cap, the container having a bottom portion extending beneath the bottom of the casing, the counter attachment comprising:

a clip with a first end and second end, the first end contacting an inner side of the casing;

a shaft housing connected to the second end of the clip;

a vertical shaft with a top end extending into the shaft housing and a bottom end extending below the shaft housing;

a foot-leg positioned beneath the fluid tank mad connected to the bottom end of the vertical shaft; and a counter having an indexing button which is located between the fluid tank and the foot-leg, wherein the button abuts against the bottom of the fluid tank and is depressed each time the tank and foot-leg are depressed.

15. The counter attachment of claim 14, wherein the vertical shaft further includes:

threads on the top end that contact mating threads on the bottom end, which enables the length of the vertical shaft to be adjustable.

16. The counter attachment of claim 14, wherein the clip further includes:

a curved portion.

17. The counter attachment of claim 14, further including:

a dimple on the clip abutting toward an opening in the casing to contact a dimple on the shaft housing.

18. A counter attachment for a spray dispenser comprising;

a clip for attachment to the dispenser:

a shaft housing connected to said clip;

a vertical shaft with top end extending into the shaft housing and a bottom end extending below said shaft housing;

a foot-leg connected to the bottom end of said vertical shaft;

threads on the top end of the vertical shaft that contact mating threads on the bottom end, which enables the length of the vertical shaft to be adjustable: and a counter having an indexing button which is depressed in response to actuation of said foot-leg each time the dispenser dispenses spray.

* * * * *